(12) United States Patent
Nakanishi

(10) Patent No.: US 6,228,036 B1
(45) Date of Patent: May 8, 2001

(54) ELECTRONIC SPHYGMOMANOMETER AND METHOD FOR MEASURING BLOOD PRESSURE

(75) Inventor: Takashi Nakanishi, Tanashi (JP)

(73) Assignee: Citizen Watch Co., Ltd., Tokyo (JP)

( * ) Notice: Subject to any disclaimer, the term of this patent is extended or adjusted under 35 U.S.C. 154(b) by 0 days.

(21) Appl. No.: 09/500,990

(22) Filed: Feb. 15, 2000

Related U.S. Application Data

(63) Continuation of application No. PCT/JP99/03704, filed on Jul. 8, 1999.

(30) Foreign Application Priority Data

Jul. 17, 1998 (JP) ................................................. 10-203507

(51) Int. Cl.$^7$ ...................................................... A61B 5/02
(52) U.S. Cl. ............................ 600/491; 600/493; 600/499
(58) Field of Search .................................... 600/481, 490, 600/491, 493–496, 499, 502, 310, 473, 477

(56) References Cited

U.S. PATENT DOCUMENTS

| | | | |
|---|---|---|---|
| 4,476,876 | * 10/1984 | Uchiyama | ............................ 600/495 |
| 5,590,662 | * 1/1997 | Hersh et al. | ........................... 600/494 |
| 5,730,139 | * 3/1998 | Miyazaki et al. | ................. 600/494 X |
| 6,106,478 | * 8/2000 | Tochikubo et al. | ............... 600/494 X |

* cited by examiner

Primary Examiner—Cary O'Connor
Assistant Examiner—Ryan Carter
(74) Attorney, Agent, or Firm—Kanesaka & Takeuchi

(57) ABSTRACT

The present invention is directed to an electronic sphygmomanometer for determining a blood pressure depending on variation in pulse wave amplitude variation waveform and cuff pressure formed by variation in the amplitude of the pulse wave, comprising: detecting the pulse wave amplitude and cuff pressure when the pulse wave exceeds a first threshold to define a first threshold; detecting the pulse wave amplitude and cuff pressure when the pulse wave exceeds a second cuff pressure to define a second point; and then, calculating a pulse wave amplitude linear equation for connecting the first and the second points to obtain a systolic blood pressure value.

According to the invention, the electronic sphygmomanometer is capable of precisely measuring a blood pressure even if dispersion occurs in pulse wave amplitude depending on how to mount the cuff or even if there is certain distortion in pulse wave depending on the physical conditions of a subject.

10 Claims, 5 Drawing Sheets

ELECTRONIC SPHYGMOMANOMETER AND METHOD FOR MEASURING BLOOD PRESSURE

CROSS REFERENCE TO RELATED APPLICATION

This is a continuation application of PCT International Application of PCT/JP99/03704 filed on Jul. 8, 1999.

TECHNICAL FIELD

The present invention relates to an electronic sphygmomanometer. In particular, the present invention relates to an electronic sphygmomanometer suitable for measuring a blood pressure by fastening a cuff to a wrist, and a method for measuring a blood pressure using this electronic sphygmomanometer.

BACKGROUND ART

In a conventional electronic sphygmomanometer, a blood pressure has been measured by fastening a cuff to an upper arm, but such measurement has been troublesome because it is required to roll up a sleeve for cuff fastening. To avoid this trouble, there has been recently proposed an electronic sphygmomanometer of a type where a cuff is fastened to a wrist. However, unlike an upper arm, a wrist has a plurality of main arteries, various pulse waves are detected depending on a cuff fastening state, resulting in poor reproducibility. Therefore, a blood pressure cannot sometimes be measured precisely depending on how to mount the cuff.

That is, like a sphygmomanometer of an arm type where the cuff is fastened to the upper arm, such sphygmomanometer of arm type where the cuff is fastened to the wrist inhibits blood stream and measures a blood pressure by compressing arteries by the cuff, and a wrist has a radial artery and an ulnar artery, and has radius and ulna bones or the like around these arteries. Thus, when a wrist is compressed by the cuff, the compressive pressure of the cuff compresses these two arteries via wrist tissues including these bones.

The pressure transmission efficiency for the cuff to compress arteries is determined depending on an artery position (a depth from a wrist surface) the artery or a positional relationship between and wrist tissues (in particular, bones or cords), and therefore, the substantial compressive pressures applied to both arteries are not always the same. In the case where the compressive pressures applied to the arteries are different from each other, a pulse wave amplitude of an artery with its poor transmission efficiency is generated as a first peak on a high-pressure side, and the pulse wave amplitude of an artery with its good transmission efficiency is generated as a second peak on a low-pressure side. Therefore, the pulse waves detected by pulse wave detecting means detects composite waves of the pulse wave amplitude of both arteries, resulting in detecting two peaks. In addition, the transmission efficiency of the compressive pressure of the cuff varies depending on a method for fastening the cuff and subjects, and thus, the obtained pulse wave amplitude is disperse and diversified, resulting in poor reproducibility.

Thus, in the case where a first-peak pulse wave is included in the pulse wave detected by the pulse wave detecting means, when the obtained pulse wave amplitude is used as it is, to determine a blood pressure value, the blood pressure value becomes high, which causes dispersion of the blood pressure values.

In addition, according to the results of investigation of 10 subjects which the inventors made, the subjects who tend to have two peaks of pulse waves, which are prone to be generated during blood pressure measurement, irrespective of the cuff fastening position, the pulse wave of the first peak was observed at a high frequency in the cuff pressure indicating the amplitude value of 50 to 80% of the maximum amplitude pulse wave on the high pressure side rather than the maximum amplitude pulse wave.

Further, the pulse wave of the first peak is detected in the case where the pressures applied to radial and ulnar arteries are substantially different from each other, but is not detected in the case where the pressures applied to both of the arteries is identical to each other. In addition, in the case where the first and the second peaks are detected immediately after only the second peak has been detected, the reproducibility of the pulse wave of the first peak is impaired.

On the other hand, the amplitude of the pulse wave of the second peak is often the maximum amplitude in general, and the pulse wave amplitude has reproducibility.

Comprehensively considering these findings, in the electronic sphygmomanometer fastening the cuff to a wrist, it is necessary to cancel the pulse wave amplitude of the first peak with poor reproducibility and calculate a blood pressure value in order to measure a precise blood pressure value with a good reproducibility.

It is one object of the present invention to provide an electronic sphygmomanometer capable of performing precise and reproducible blood pressure measurement even in the case where distortion occurs with detected pulse waves depending on how to mount the cuff as in an electronic sphygmomanometer, and in particular, a sphygmomanometer of cuff type where the cuff is fastened to the wrist or in the case where there is certain distortion with the detected pulse waves depending on the physical conditions of a subject; and a method for measuring a blood pressure using this sphygmomanometer.

DISCLOSURE OF THE INVENTION

To achieve the aforementioned object, an electronic sphygmomanometer according to the present invention comprises: a cuff for applying a pressure to blood vessels; cuff pressure adjusting means for adjusting a pressure in the cuff; pressure signal converting means for outputting as a pressure signal the cuff internal pressure when the pressure applied to blood vessels by the cuff pressure adjusting means is reduced; pulse wave detecting means for detecting pulse waves from said pressure signal; cuff pressure detecting means for detecting the pressure in the cuff from said pressure signal; and blood pressure determining means for determining the pressure in said cuff and the blood pressure from said pulse wave, wherein said blood pressure determining means is composed of: first pulse wave detecting means for detecting as a first pulse wave amplitude value a pulse wave amplitude firstly exceeding a first threshold from said pulse waves; second pulse wave detecting means for detecting as a second pulse wave amplitude value a pulse wave amplitude firstly exceeding a pulse wave amplitude a second threshold; first cuff pressure detecting means for detecting a first cuff pressure value when said first pulse wave amplitude value is detected; second cuff pressure detecting means for detecting a second cuff pressure value when said second pulse wave amplitude value; a linear equation calculating means of the pulse wave amplitude for linearly equating a relationship between a cuff pressure and a pulse wave amplitude based on said first pulse wave amplitude value, said second pulse wave amplitude value, said first cuff pressure value, and said second cuff pressure value, and blood pressure calculating means for obtaining a systolic blood pressure value from the pulse wave amplitude linear equation.

In addition, a method for measuring a blood pressure according to the present invention is directed to a blood pressure measuring method for determining a blood pressure depending on pulse wave amplitude variation waveforms formed by variation of the amplitude of pulse waves and variation in the cuff pressure, wherein the pulse wave amplitude and cuff pressure is detected when said pulse wave exceeds a thirst threshold, and is defined as a first point, the pulse wave amplitude and cuff pressure is detected when said pulse wave exceeds a second threshold, and is defined as a second point, and then a pulse wave amplitude linear equation connecting these first and second points is calculated, and a systolic blood pressure value is obtained based on this pulse wave amplitude linear equation.

An electronic sphygmomanometer and method for measuring a blood pressure of the present invention comprising such arrangement and means, is capable of measuring a blood pressure precisely, even if dispersion occurs with pulse wave amplitudes depending on how to mount the cuff as in the electronic sphygmomanometer of such type where the cuff is fastened to the wrist or even if there is certain dispersion with pulse waves depending on the physical conditions of a subject.

BEST MODE FOR CARRYING OUT OF THE INVENTION

Figure 1:
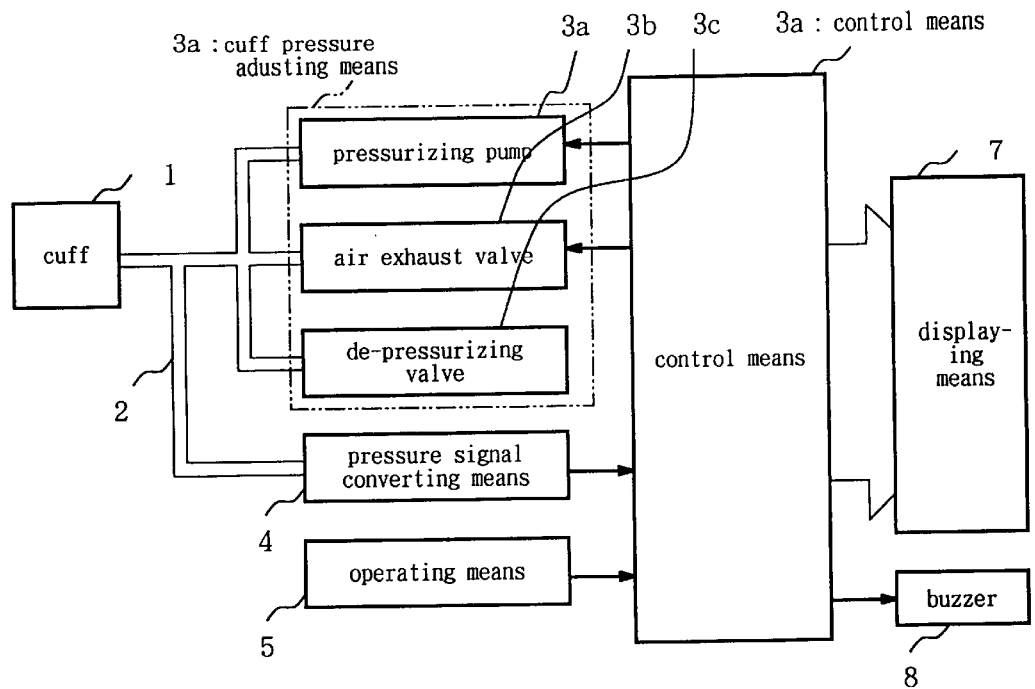
FIG. 1 shows a block diagram of an electronic sphygmomanometer according to a preferred embodiment of the present invention.
Figure 2:
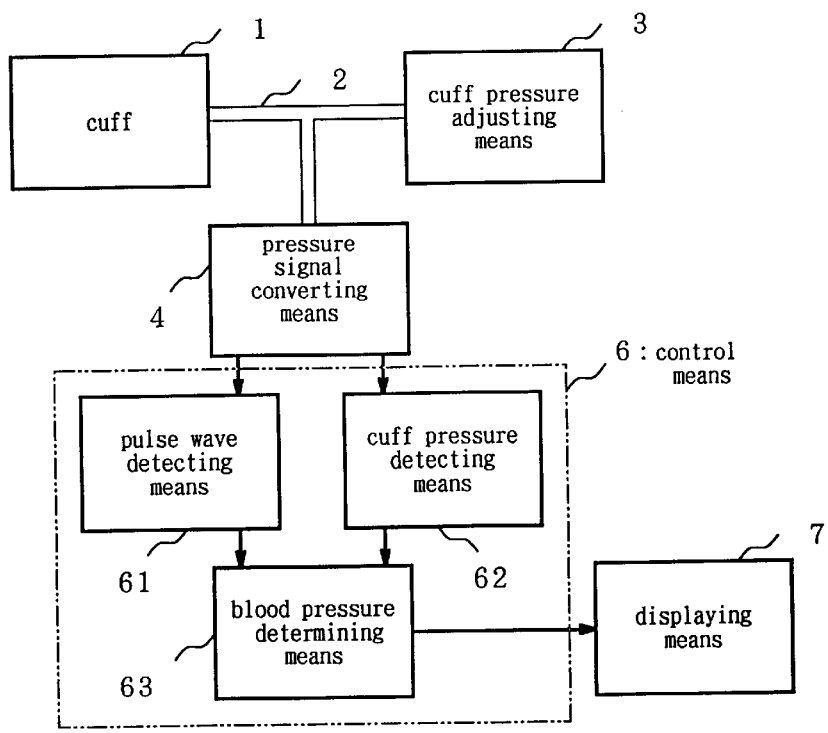
FIG. 2 shows a block diagram of essential portions in FIG. 1.

An electronic sphygmomanometer shown in FIG. 1 has a cuff 1, cuff pressure adjusting means 3, pressure signal converting means 4, operating means 5, control means 6, and displaying means 7.

The cuff 1 is a bag for applying a pressure to a subject's wrist, there by to tighten the subject's blood vessels, and is connected to the cuff pressure adjusting means 3 and the pressure signal converting means 4 by means of a tube 2.

The cuff pressure adjusting means 3 is composed of a pressurizing pump 3a for applying the subject's wrist by supplying air to the cuff 1; an exhaust valve 3b for exhausting the air in the cuff 1; and a de-pressurizing valve 3c for reducing the air pressure in the cuff at a constant speed.

The pressure signal converting means 4 detects the pressure in the cuff 1, and converts it to an electrical signal. The pressurizing pump 3a, the exhaust valve 3b, and the pressure signal converting means 4, respectively, are connected to the control means 6. In addition, the operating means 5, the displaying means 7, and a buzzer 8 are connected to the control means 6.

The control means 6 has a storage means such as a CPU, a ROM, a RAM, and has pulse wave detecting means 61, cuff pressure detecting means 62, and blood pressure determining means 63. Here, the pulse wave detecting means 61 detects a pulse wave based on the pressure signal from the pressure signal converting means 4, and detects the scale of the pulse wave amplitude. In addition, the cuff detecting means 62 detects a cuff pressure based on the pressure signal from the pressure signal converting means 4. Further, the blood pressure determining means 63 receives signals from the pulse wave detecting means 61 and the cuff pressure detecting means 62, and determines a blood pressure depending on a pulse wave amplitude and the cuff pressure corresponding to the pulse wave amplitude.

In this electronic sphygmomanometer, an operator mount the cuff 1 to the subject's wrist so as to tighten the subject's blood vessels, and operates the operating means 5 to turn ON a power source. Thereby control means 6 causes the pressure signal converting means 4 to start detecting the pressure in the cuff 1, by turning ON the power source, and output a pressure signal. In addition, when a blood measuring is started is instructed by means of the operating means 5, the control means 6 starts up a pressurizing pump 3a to supply air to the cuff 1. Then, when the pressure in the cuff 1 reaches a pressurization set value stored in a RAM, the pressurizing pump 3a is deactivated, and then, the air in the cuff 1 is gradually discharged and depressurized by means of a depressurizing valve 3c.

Figure 4:
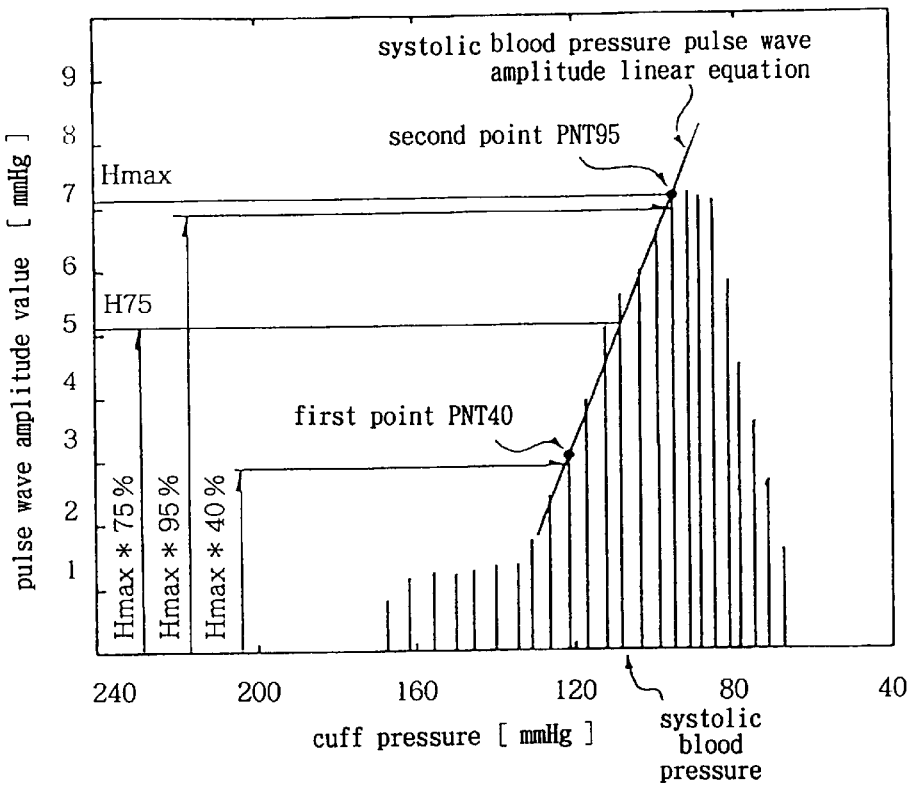
FIG. 4 is a graph showing a relationship between a standard cuff pressure and a pulse wave amplitude value, wherein an calculation example of linear equation of the systolic blood pressure pulse wave amplitude is shown.

With depressurization, the pressure in the cuff 1 is reduced, the subject's blood vessels are loosened, and the blood commence to flow. When the blood vessels are loosened, and the blood pressure is close to a systolic blood pressure, the blood vessels start pulsation. Therefore, the pulse wave detecting means 61 interlocks with heart beats, and detects pulse wave amplitudes. As shown in FIG. 4, the pulse wave amplitude gradually increases with an decrease in the cuff pressure. When the pressured blood vessels compressed by the cuff is loosened, thereby returning to the normal blood flow, the pulse wave amplitude acutely decreases, and is not detected. The blood pressure determining means 63 determines a blood pressure depending on the pulse wave amplitude that varies with a decrease in the cuff pressure and the cuff pressure corresponding to this varying pulse wave amplitude.

Figure 3:
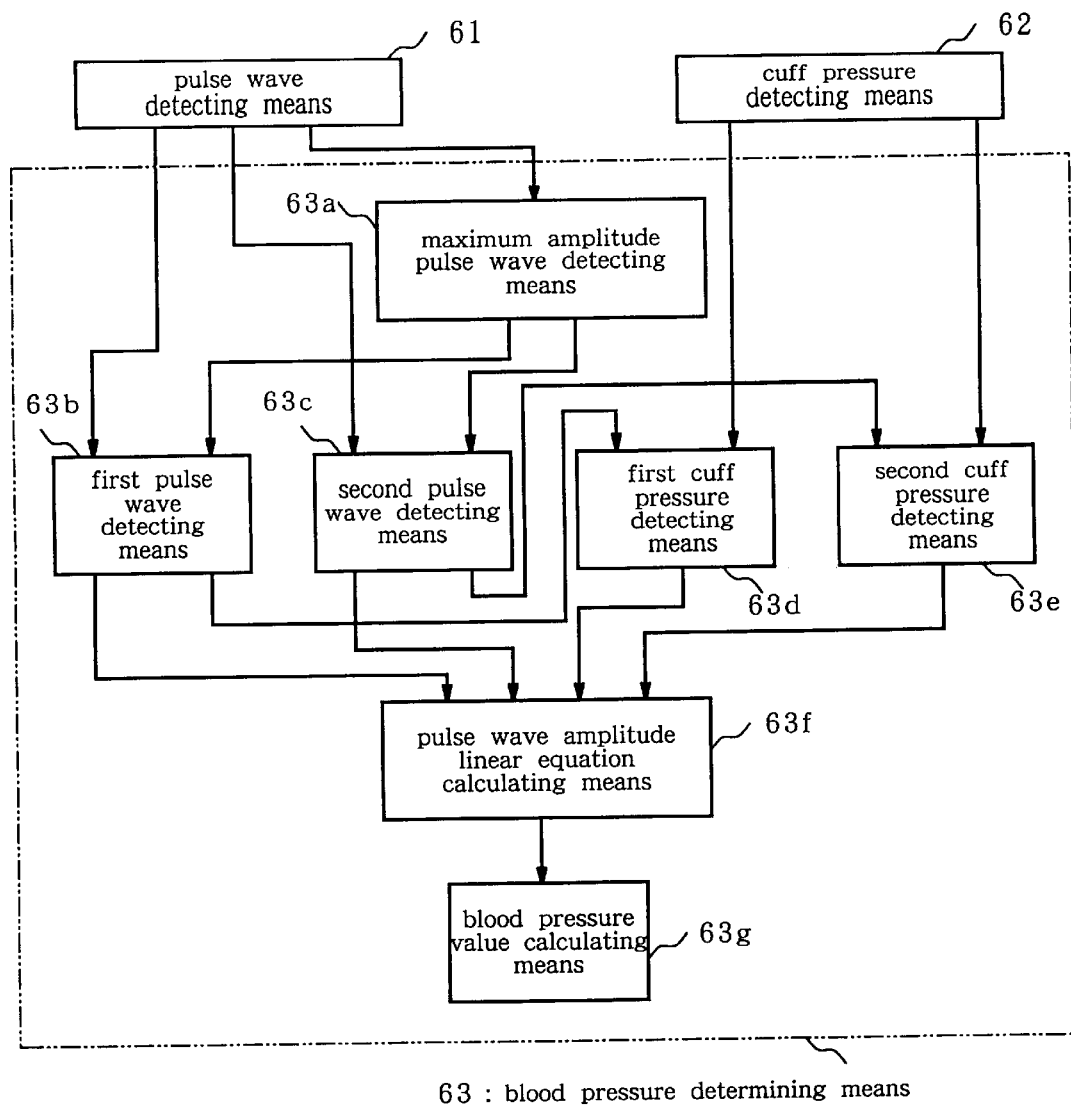
FIG. 3 shows a block diagram of essential portions in FIG. 2.

Next, the constitution and function of the blood pressure determining will be described in detail with reference to FIG. 3 and FIG. 4.

The blood pressure determining means 63 comprises maximum amplitude pulse wave detecting means 63a, first and second pulse wave detecting means 63b and 63c, first and second cuff pressure detecting means 63d and 63e, pulse wave amplitude linear equation detecting means 63f, and blood pressure value calculating means 63g.

Here, the maximum amplitude pulse wave detecting means 63a detects a maximum amplitude wave pulse from among the pulse waves detected by the pulse wave detecting means 61. From among the pulse waves detected by the pulse wave detecting means 61, the first pulse wave detecting means 63b detects as a first pulse wave amplitude value a pulse wave amplitude value firstly exceeding a first threshold which is 40% of the amplitude value of the maximum amplitude pulse wave on a high pressure side rather than the maximum amplitude pulse wave. From among the pulse waves of the maximum amplitude pulse wave, the second pulse wave detecting means 63c detects as a second pulse wave amplitude value a pulse wave amplitude firstly exceeding a second threshold which is 95% of the amplitude value of the maximum amplitude pulse wave on the high pressure side rather than the maximum amplitude pulse wave.

In this embodiment, the first threshold is set to, e.g., 40% of the amplitude value of the maximum amplitude pulse wave; and however, another optimum value may exist within the range of 0% to 50% depending on the device types. Similarly, the second threshold is set to, e.g., 95% of the amplitude value of the maximum amplitude; and however, another optimum value may exist within the range of 80% to 100% depending on the device types, thus making it possible to appropriately change the first and the second thresholds.

The first cuff pressure detecting means 63d uses cuff pressure detecting means 62, thereby to detect a first cuff pressure value during first pulse wave detection; and the second cuff pressure value detecting means 63e uses cuff pressure detecting means 62, thereby to detect a second cuff pressure value during second pulse wave detection. As shown in FIG. 4, linear equation calculating means 63f of the pulse wave amplitude calculates a pulse wave amplitude linear equation for connecting a first point PNT40 obtained from the first pulse wave amplitude value and the first cuff pressure value to a second point PNT95 obtained from the second pulse wave amplitude value and said second cuff pressure value, thereby to obtain a relationship between the cuff pressure and the pulse wave amplitude.

In FIG. 4, assuming that the longitudinal axis, i.e., pulse wave amplitude value is Y, and the transverse axis, i.e., cuff pressure is X, the pulse wave amplitude linear equation is as follows:

$$Y=aX+b \qquad (1)$$

In general, to obtain the blood pressure value, the equation (1) is deformed as follows, and is used.

$$X=(Y-b)/a \qquad (2)$$

An operation of blood pressure detection is performed by means of blood pressure calculating means 63g. In FIG. 4, a systolic blood pressure is determined by a cuff pressure of a pulse wave amplitude of a constant ratio to the maximum amplitude.

As shown in FIG. 4, a value of a cuff pressure P75 in a pulse wave amplitude value H75 of 75% of the maximum pulse wave amplitude value Hmax, which is a pulse wave amplitude value of the maximum amplitude pulse wave on linear equation of the pulse wave amplitude in the systolic blood pressure, is a systolic blood pressure. Therefore, the systolic blood pressure value X is obtained by substituting 75% of Hmax for Y of the equation (2):

$$X=(0.75\times Hmax-b)/a \qquad (3)$$

An embodiment shown in FIG. 4 is a case of a subject having a relationship between a standard cuff pressure and a pulse wave amplitude value. Even in a relationship between cuff pressure and pulse wave amplitude value which are not standard as shown in FIG. 4 and FIG. 5, it is possible to measure a blood pressure in a similar manner as in FIG. 4.

Figure 5:
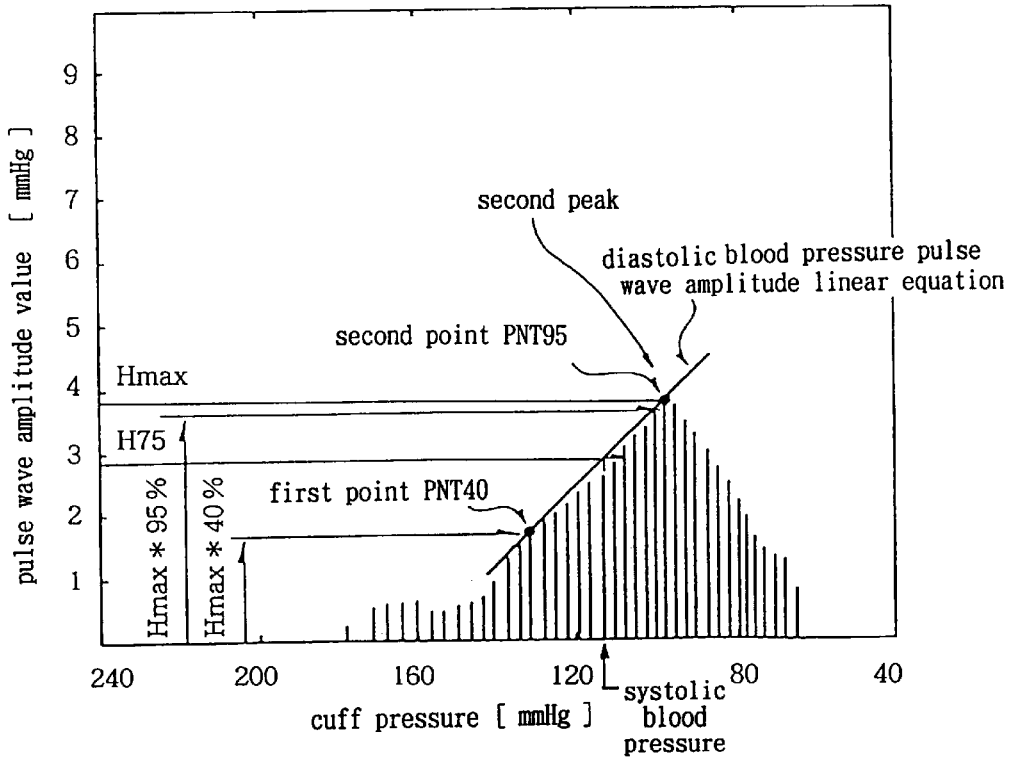
FIG. 5 is a graph showing a relationship between a cuff pressure and a pulse wave amplitude value having only a second peak in a subject who has no reproducibility in the pulse wave amplitude, wherein an example of linear equation of the systolic blood pressure pulse wave amplitude is shown.
Figure 6:
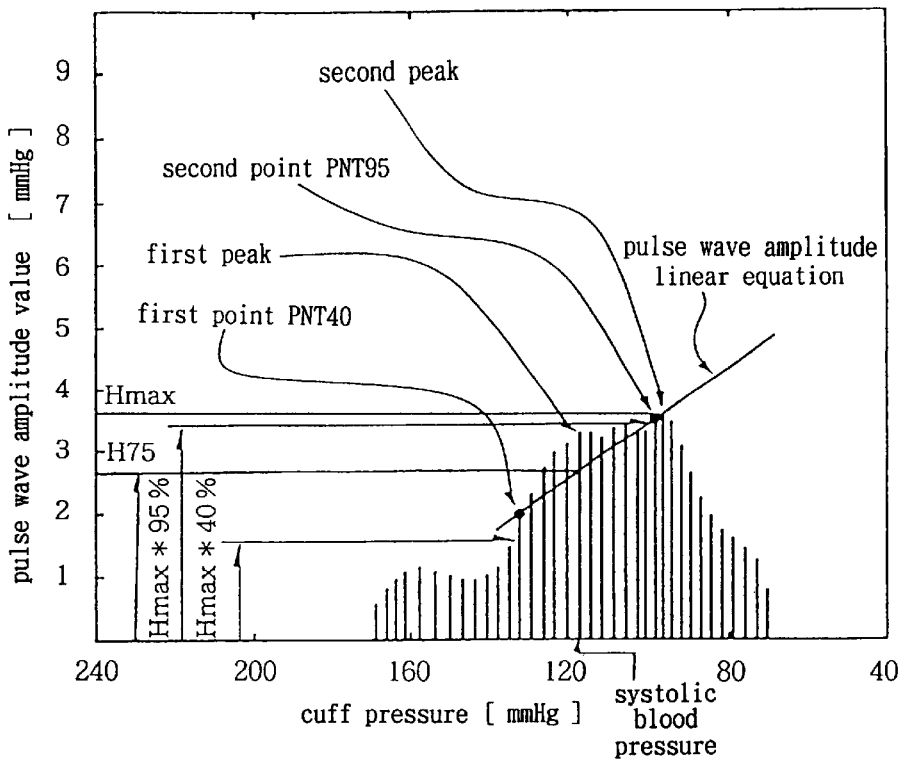
FIG. 6 is a characteristic graph of a systolic blood pressure showing a relationship between a cuff pressure and a pulse wave amplitude value having first and second peaks in a subject who has no reproducibility in the pulse wave amplitude, wherein a calculation example of linear equation of the systolic blood pressure pulse wave amplitude is shown.

That is, when the pulse wave has only a second peak without good reproducibility, as shown in FIG. 5, a linear equation of a systolic blood pressure pulse wave amplitude as shown in FIG. 5 is obtained, and a blood pressure value can be determined. Similarly, when the pulse wave has first and second peaks without reproducibility, as shown in FIG. 6, a systolic blood pressure pulse wave amplitude linear equation shown in FIG. 6 is obtained, and a blood pressure value can be determined.

A diastolic blood pressure is obtained from the pulse wave amplitude in an area of the low-pressure side rather than the maximum amplitude. In this area since a peak does not appear, and reproducibility is good, the diastolic blood pressure can be obtained from the cuff pressure of the pulse wave amplitude of a constant ratio to the maximum pulse wave amplitude value. In general, this ratio is set to 75%, and the diastolic blood pressure is calculated as a value of the cuff pressure of P75 when the pressure becomes lower than 75% of Hmax.

However, when a pulse wave amplitude linear equation is obtained in a similar way as the systolic blood pressure, and the diastolic blood pressure is calculated from this equation, more reproducible results can be obtained.

Next, a method for determining a diastolic blood pressure using a pulse wave amplitude linear equation will be described. The maximum amplitude pulse wave detecting means 63a detects a maximum amplitude pulse wave from among the pulse waves detected by the pulse wave detecting means 61. From among of the pulse waves detected by the pulse wave detecting means 61, the first pulse wave detecting means 63b detects as a third pulse wave amplitude value a pulse wave which firstly becomes lower than a third threshold which is 40% of the amplitude value of the maximum amplitude pulse wave on the low pressure side rather than the maximum amplitude pulse wave. From among the pulse waves detected by the pulse wave detecting means 61, the second pulse wave detecting means 63c detects as a fourth pulse wave amplitude value a pulse wave which firstly becomes lower than a fourth threshold which is 95% of the amplitude value of the maximum amplitude pulse wave on the low pressure side rather than the maximum amplitude pulse wave.

In this embodiment, as is the case with the systolic blood pressure, the third threshold value is set to 40% of the amplitude value of the maximum amplitude wave pulse, but another optimum value may exist within the range of 0% to 50% depending on the device types. Similarly, the fourth threshold is set to 95% of the amplitude value of the maximum amplitude pulse wave, but another optimum value may exist within the range of 80% to 100% depending on the device types, thus making it possible to appropriately change first and second thresholds.

Figure 7:
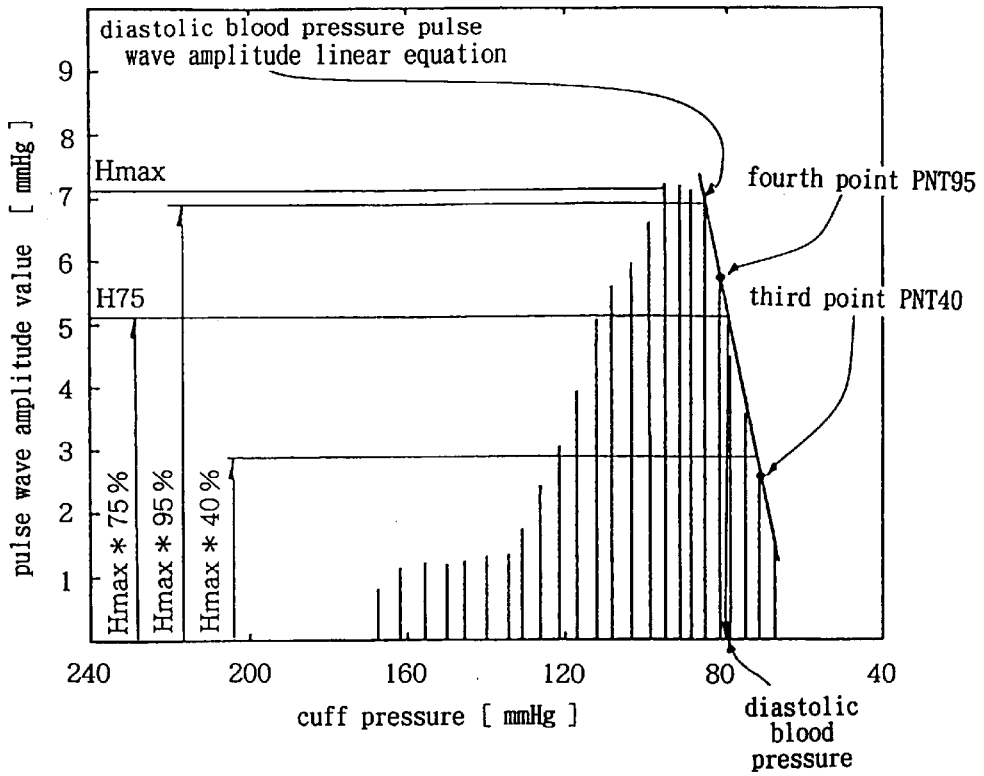
FIG. 7 is a characteristic graph of a diastolic blood pressure showing a standard cuff pressure and a pulse wave amplitude value, wherein a calculation example of the diastolic blood pressure pulse wave linear equation is shown.

The first cuff pressure detecting means 63d uses the cuff pressure detecting means 62, thereby to detect a third cuff pressure value during third pulse wave detection; and the second cuff pressure detecting means 63e uses the cuff pressure detecting means, thereby to detect a fourth cuff pressure value during fourth pulse wave detection. As shown in FIG. 7, a diastolic blood pressure pulse wave amplitude linear equation is obtained by the linear equation calculating means 63f of the pulse wave amplitude, and connects a third point PNT40 obtained from the third pulse wave amplitude value and the third cuff pressure value; and a fourth point PNT95 obtained from the fourth pulse wave amplitude value and the fourth cuff pressure value, thereby to obtain a relationship between the cuff pressure and the pulse wave amplitude.

By the blood pressure value calculating means 63g, the procedure for determining the diastolic blood pressure from the diastolic blood pressure pulse wave amplitude linear equation can be performed in a same manner as that for determining the systolic blood pressure from the systolic blood pressure pulse wave amplitude linear equation.

In this embodiment, it is described the ratio for determining the systolic and diastolic blood pressures is set to 75% of the maximum pulse wave amplitude value of Hmax. However, another optimum value may exist depending on the device types. In addition, the ratio may be properly changed according to pulse wave data such as the cuff pressure indicating the maximum amplitude or the entire shape of the pulse wave amplitude, thereby making it possible to calculate the blood pressure value from the linear equation of the pulse wave amplitude.

Further, it is described that the first pulse wave amplitude value is assumed as pulse wave amplitude value exceeding the first threshold and the second pulse wave amplitude value is assumed as pulse wave amplitude value exceeding the second threshold. However, they can be assumed as pulse wave amplitude value close to the first and the second thresholds. Similarly, it is described that the third and fourth pulse wave amplitude values are pulse wave amplitude values which are lower than the third and fourth thresholds. However, they can be pulse wave amplitude values close to the third and fourth thresholds.

EXAMPLE

Figure 8:
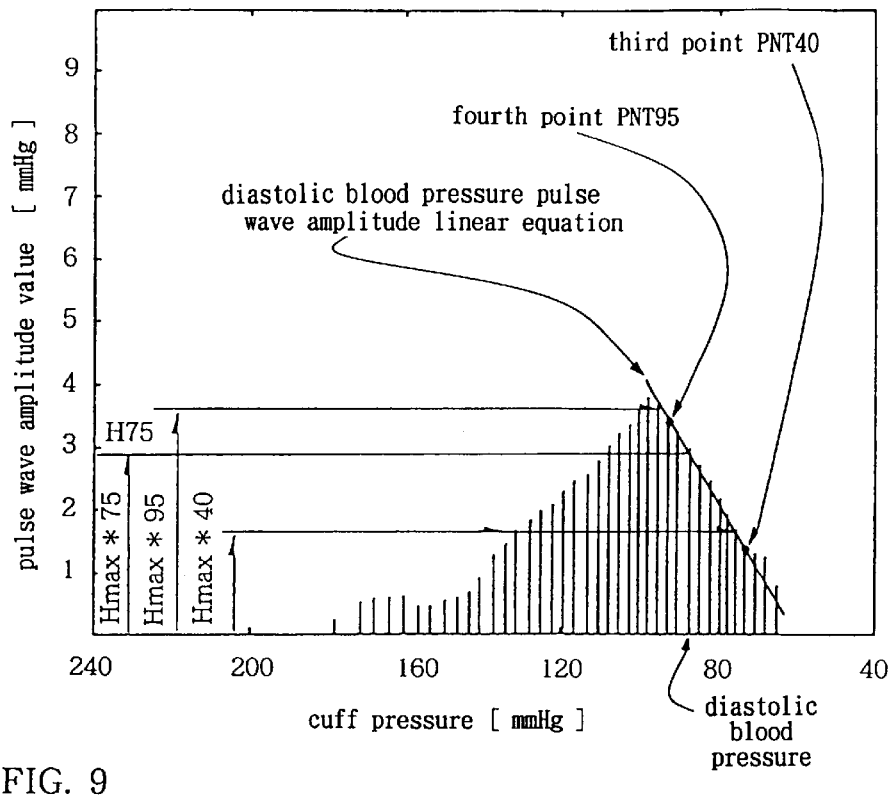
FIG. 8 is a characteristic graph of a diastolic blood pressure showing a relationship between a cuff pressure and a pulse wave amplitude value having only a second peak in a subject who has no reproducibility in the pulse wave amplitude, wherein the diastolic blood pressure pulse wave amplitude pulse wave linear equation is shown.
Figure 9:
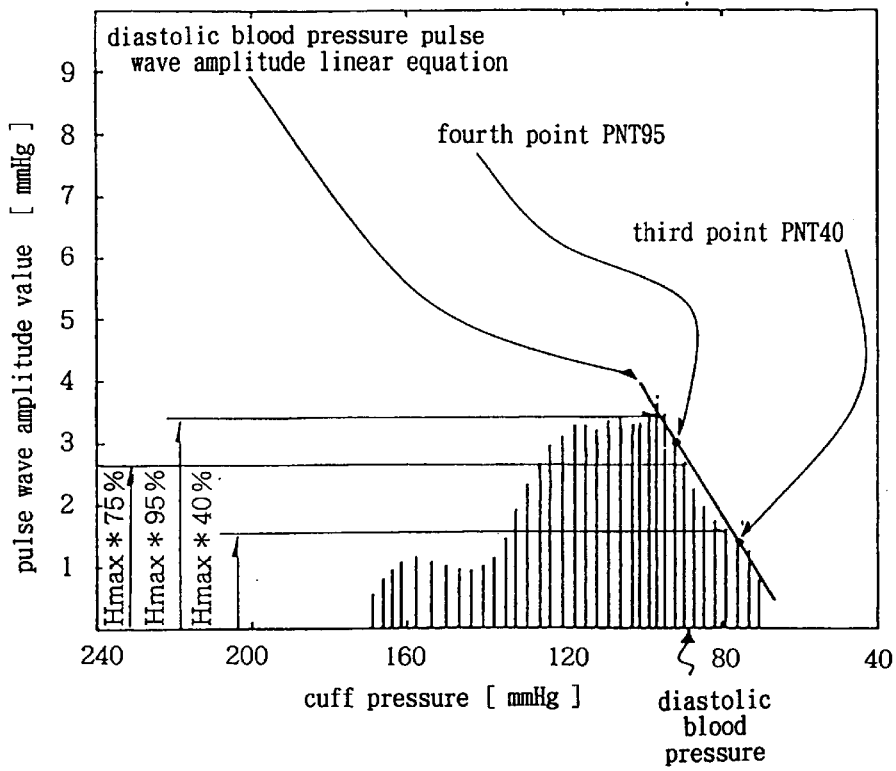
FIG. 9 is a graph of showing a relationship between a cuff pressure and a pulse wave amplitude value having first and second peaks in a subject who has no reproducibility in the pulse wave amplitude, wherein a calculation example of the diastolic blood pressure pulse wave amplitude linear equation is shown.

The following table shows the comparison results when there were measured by auscultation the systolic/diastolic blood pressure values in a first example (FIG. 5 and FIG. 8) and second example (FIG. 6 and FIG. 9) when the values were measured by using the electronic sphygmomanometer of the present invention and a conventional electronic sphygmomanometer. In the first example, the systolic/diastolic blood pressure values have only a second peak without reproducibility in the pulse wave amplitude. In the second embodiment, the systolic/diastolic blood pressure values have the first and the second peaks without reproducibility.

|  | Auscultation | The present invention | Conventional |
|---|---|---|---|
| First embodiment (FIG. 5 and FIG. 8) | 116/88 | 113/87 | 107/83 |
| Second embodiment (FIG. 6 and FIG. 9) | 116/88 | 117/88 | 126/89 |
| Difference | 0/0 | 4/1 | 19/6 |

This table shows that when the electronic sphygmomanometer of the present invention is used, precise blood pressure measurement can be performed in a similar manner as blood pressure measurement using auscultation.

INDUSTRIAL APPLICABILITY

The present invention is widely applicable to an electronic sphygmomanometer for measuring a blood pressure by fastening a cuff to a wrist or any other site where an obstacle is present.

What is claimed is:

1. An electronic sphygmomanometer comprising a cuff for applying a pressure to blood vessels; cuff pressure adjusting means for adjusting a pressure in the cuff; pressure signal converting means for outputting as a pressure signal the cuff internal pressure appeared when the pressure applied to the blood vessels is depressurized by means of the cuff pressure adjusting means; pulse wave detecting means for detecting a pulse wave from said pressure signal; cuff pressure detecting means for detecting the pressure in the cuff from said pressure signal; and blood pressure determining means for determining the pressure in said cuff and the blood pressure from blood said pulse wave, said electronic sphygmomanometer meter being characterized in that said blood pressure determining means comprises: first pulse wave detecting means for detecting as a first pulse wave amplitude value a pulse wave amplitude firstly exceeding a first threshold from among said pulse waves; second pulse wave detecting means for detecting as a second pulse wave amplitude value a pulse wave amplitude firstly exceeding a second threshold; first cuff pressure detecting means for detecting a first cuff pressure value when said first pulse wave amplitude value is detected; second cuff pressure detecting means for detecting a second cuff pressure value when said second pulse wave amplitude value is detected; a linear equation calculating means of the pulse wave amplitude for linearly equating a relationship between a cuff pressure and a pulse wave amplitude based on said first pulse wave amplitude value, said second pulse wave amplitude value, said first cuff pressure value, and said second cuff pressure value; and a blood pressure calculating means for obtaining a systolic blood pressure value from a linear equation of pulse wave amplitude.

2. An electronic sphygmomanometer according to claim 1, characterized in that said first threshold is 0% to 50% of the maximum pulse wave amplitude value.

3. An electronic sphygmomanometer according to claim 1, characterized in that said second threshold is 80% to 100% of the maximum pulse wave amplitude value.

4. An electronic sphygmomanometer according to claim 1 characterized in that said first pulse wave detecting means detects as a third pulse wave amplitude value a pulse wave amplitude which firstly becomes lower than a third threshold value; said second pulse wave detecting means detects as a fourth pulse wave amplitude value a amplitude which becomes firstly lower than a fourth threshold; said first cuff pressure detecting means detects a third cuff pressure a cuff pressure when said third pulse wave amplitude value is detected; said second cuff pressure detecting means detects as a fourth cuff pressure a cuff pressure when said fourth pulse wave amplitude value is detected; said linear equation calculating means of the pulse wave amplitude linearly equates a relationship between the cuff pressure and the pulse wave amplitude from said third pulse wave amplitude value, said fourth pulse wave amplitude value, said third cuff pressure value, and said fourth cuff pressure value; and said blood pressure calculating means obtains a diastolic blood pressure value from the pulse wave amplitude linear equation.

5. An electronic sphygmomanometer according to claim 4, characterized in that said third threshold is 0% to 50% of the maximum pulse wave amplitude linear equation.

6. An electronic sphygmomanometer according to claim 4, characterized in that said threshold is 80% to 100% of the maximum pulse wave amplitude value.

7. An electronic sphygmomanometer according to claim 1, characterized in that said pulse wave amplitude linear equation is used, thereby to substitute the pulse wave amplitude of a constant ratio for the maximum amplitude pulse wave value and determine a blood pressure value.

8. An electronic sphygmomanometer according to claims 1, characterized in that said blood pressure value calculating means uses said pulse wave amplitude linear equation, thereby to change a ratio for the maxim um amplitude for determining a blood pressure value for the maximum amplitude value based on pulse wave data.

9. A blood pressure measuring method for determining a blood pressure depending on variation in a pulse wave amplitude variation waveform and a cuff pressure formed by variation in the amplitude of the pulse wave, said blood pressure measuring method characterized by comprising: detecting the pulse wave amplitude and cuff pressure when said pulse wave exceeds a first threshold to define a first point, and detecting the pulse wave amplitude and cuff pressure when said pulse wave exceeds a second threshold to define a second point; and then, calculating a pulse wave amplitude linear equation for connecting the first and the second points to obtain a systolic blood pressure value based on the pulse wave amplitude linear equation.

10. A blood pressure measuring method for determining a blood pressure depending on variation in the pulse wave amplitude variation waveform and cuff pressure formed by variation in the amplitude of the pulse wave, said blood pressure measuring method characterized by comprising: detecting the pulse wave amplitude and cuff pressure when said pulse wave becomes lower than a third threshold to define a third point, and detecting the pulse wave amplitude and cuff pressure when said pulse wave becomes lower than a fourth threshold to define a fourth point; and then, calculating a pulse wave amplitude linear equation for connecting the third and fourth points to obtain a diastolic blood pressure value based on the pulse wave amplitude linear equation.

* * * * *